United States Patent
Louis et al.

(10) Patent No.: US 9,649,199 B2
(45) Date of Patent: *May 16, 2017

(54) VERTEBRAL CAGE DEVICE WITH MODULAR FIXATION

(71) Applicant: LDR Medical, Rosières Près Troyes (FR)

(72) Inventors: Christian Louis, Aubagne (FR); Jean Huppert, L'etrat (FR); Patrick Tropiano, Marseilles (FR); Thierry Dufour, Olivet (FR)

(73) Assignee: LDR Medical, Sainte-Savine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/798,900

(22) Filed: Jul. 14, 2015

(65) Prior Publication Data

US 2016/0008142 A1    Jan. 14, 2016

Related U.S. Application Data

(63) Continuation of application No. 13/438,352, filed on Apr. 3, 2012, now Pat. No. 9,078,765, which is a
(Continued)

(51) Int. Cl.
*A61F 2/44* (2006.01)
*A61B 17/86* (2006.01)
(Continued)

(52) U.S. Cl.
CPC ............ *A61F 2/4455* (2013.01); *A61B 17/86* (2013.01); *A61F 2/4465* (2013.01); *A61B 17/0642* (2013.01); *A61B 17/7059* (2013.01);

*A61B 2017/0648* (2013.01); *A61F 2002/2835* (2013.01); *A61F 2002/305* (2013.01); *A61F 2002/3008* (2013.01);
(Continued)

(58) Field of Classification Search
CPC . A61B 17/86; A61B 17/0642; A61B 17/7059; A61B 2017/0648; A61F 2/4455; A61F 2/4465; A61F 2230/0034; A61F 2230/0013; A61F 2002/2835; A61F 2002/3008; A61F 2002/30131; A61F 2002/30472; A61F 2002/305; A61F 2002/30575; A61F 2002/30604; A61F 2002/448; A61F 2002/4475; A61F 2220/0025; A61F 2220/0041; A61F 2250/0098
USPC .............................. 606/246, 247, 280, 329; 623/17.11–17.16
See application file for complete search history.

(56) References Cited

U.S. PATENT DOCUMENTS 5,397,364 A * 3/1995 Kozak .................. A61B 17/025
606/247
6,447,546 B1 * 9/2002 Bramlet .................. A61F 2/446
623/17.11
(Continued)

*Primary Examiner* — Pedro Philogene
(74) *Attorney, Agent, or Firm* — Lauff Law PLLC

(57) ABSTRACT

Intervertebral arthrodesis for insertion in an intervertebral space separating opposite faces of two adjacent vertebrae has a ring shaped intervertebral cage having a bar that extends perpendicular to the axis of the spine. The bar has a height less than the rest of the cage. A surface of the cage contacting the vertebrae has an undulating shape for limiting sliding of the cage in a plane parallel to the vertebrae faces.

20 Claims, 5 Drawing Sheets

Related U.S. Application Data continuation of application No. 12/430,768, filed on Apr. 27, 2009, now Pat. No. 8,147,556, which is a continuation of application No. 10/483,563, filed as application No. PCT/IB02/03390 on Jul. 12, 2002, now Pat. No. 7,594,931.

(51) Int. Cl.
   *A61B 17/064* (2006.01)
   *A61B 17/70* (2006.01)
   *A61F 2/28* (2006.01)
   *A61F 2/30* (2006.01)

(52) U.S. Cl.
   CPC ............... *A61F 2002/30131* (2013.01); *A61F 2002/30472* (2013.01); *A61F 2002/30578* (2013.01); *A61F 2002/30604* (2013.01); *A61F 2002/448* (2013.01); *A61F 2002/4475* (2013.01); *A61F 2220/0025* (2013.01); *A61F 2220/0041* (2013.01); *A61F 2230/0013* (2013.01); *A61F 2230/0034* (2013.01); *A61F 2250/0098* (2013.01)

(56) References Cited

U.S. PATENT DOCUMENTS

| | | | |
|---|---|---|---|
| 6,964,687 B1 * | 11/2005 | Bernard | A61F 2/447 623/17.11 |
| 7,594,931 B2 * | 9/2009 | Louis | A61B 17/86 606/247 |
| 8,147,556 B2 * | 4/2012 | Louis | A61B 17/86 623/17.16 |
| 8,267,999 B2 * | 9/2012 | Beaurain | A61F 2/442 623/17.11 |
| 9,078,765 B2 * | 7/2015 | Louis | A61B 17/86 |

\* cited by examiner

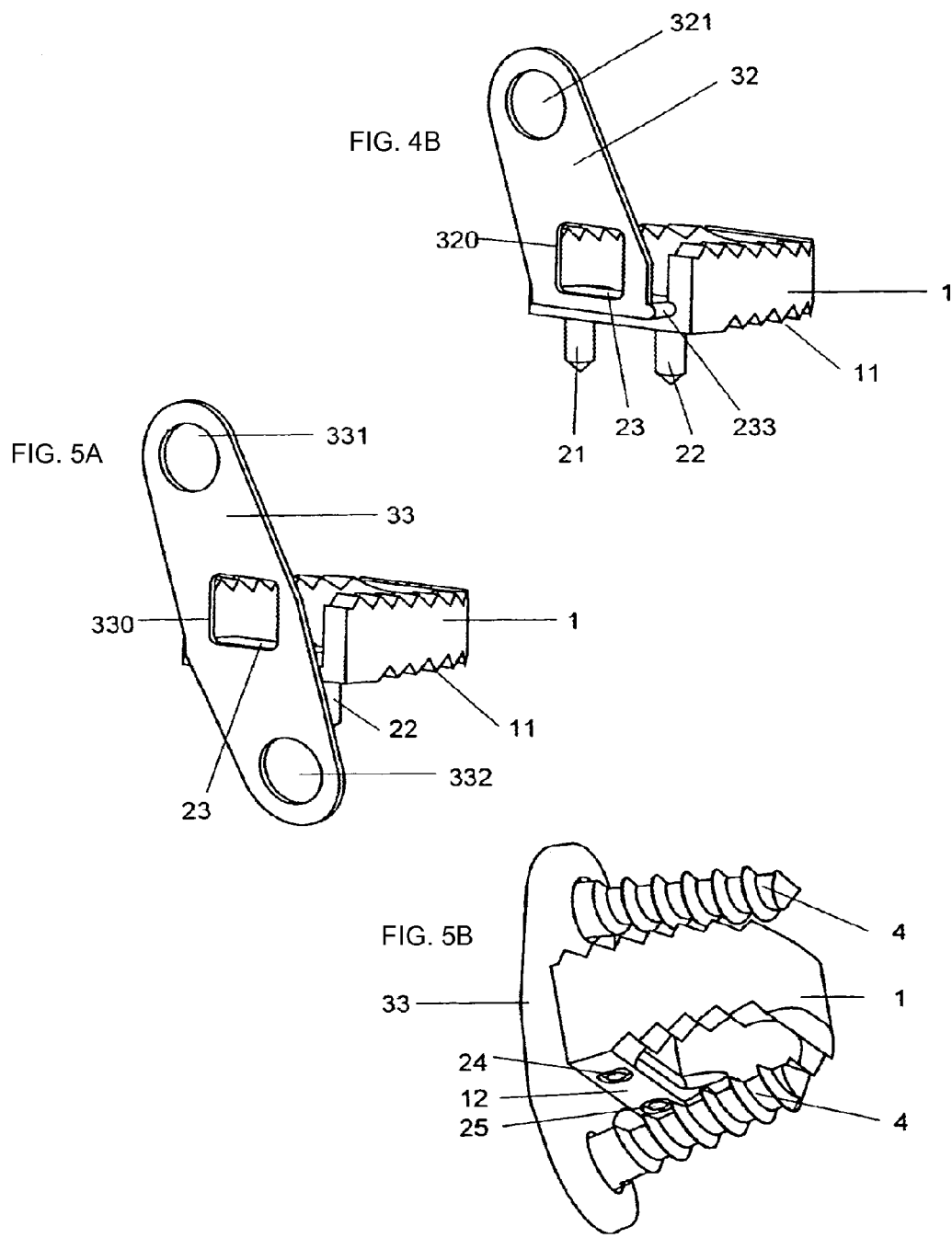

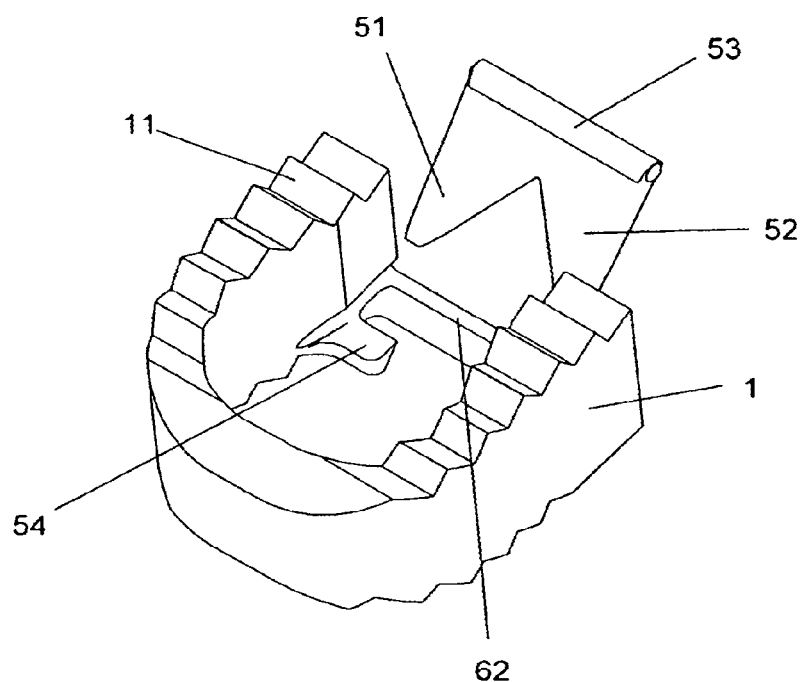

VERTEBRAL CAGE DEVICE WITH MODULAR FIXATION

CROSS-REFERENCE TO RELATED APPLICATIONS

This application is a continuation of U.S. patent application Ser. No. 13/438,352, filed Apr. 3, 2012, and issuing as U.S. Pat. No. 9,078,765 on Jul. 14, 2015, which is a continuation of U.S. patent application Ser. No. 12/430,768, filed Apr. 27, 2009, and issuing as U.S. Pat. No. 8,147,556 on Apr. 3, 2012, which is a continuation of U.S. patent application Ser. No. 10/483,563, having a 371(c) date of May 21, 2004, and issuing as U.S. Pat. No. 7,594,931 on Sep. 29, 2009, which is a National Stage entry of International Application PCT/IB02/03390, filed Jul. 12, 2002, which claims priority to French Patent Application No. 01/09381, filed Jul. 13, 2001.

BACKGROUND

The present invention concerns an arthrodesis device, used to enable fusing of two contiguous vertebrae by development of bony tissues with replacement of fibrocartilaginous discs ensuring the bonding between the vertebrae of the vertebral column or the end of the latter.

The intervertebral discs are formed from a deformable but not compressible part called "nucleus pulposus" containing approximately 80% water, surrounded by several elastic fibrous layers uniting to maintain the nucleus, absorbing part of the forces applied to the disc unit, and stabilizing the articulation. These parts may often be degraded by compression, displacement or wear and tear, following shocks, infections, exaggerated forces or simply over time. The degradation of this articulation part may cause intense pain in the patient and significant discomfort.

SUMMARY

In a good number of cases, the treatment consists of removing all or part of the damaged intervertebral disc and connecting the vertebrae concerned by causing bony fusion between them. To do that, one places between the vertebrae an artificial structure allowing their separation to be maintained, while with it introducing into the intervertebral space either a bony graft or a bony substitute, compounded material that will be invaded by the growth of adjacent bony tissues. This structure often takes the shape of an open or closed ring called cage, and may be positioned on the basis of a cage by the intervertebral space in the case of cervical vertebrae, or on the basis of one or two cages by the intervertebral space in the case of lumbar vertebrae. This positioning is done most often by the anterior surface of the vertebrae in the case of a cervical cage, or by the antero-lateral surface of the vertebrae (one cage) or posterior (two cages) of vertebrae in the case of a lumbar cage. As for grafts and bony substitutes, they are introduced in the cage either before or after its positioning and are therefore found in contact with the two vertebrae surrounding the treated intervertebral space.

During the time necessary for growth and up to the reinforcement of arthrodesis, which may be on the order of six months, it is important that the various movements of forces taking place in the intervertebral space do not cause displacement of the cage, which would then risk deteriorating the bony tissues during formation or even escaping outside this space and damaging the adjacent organs.

To avoid such displacements, a solution used consists of equipping the surfaces of the cage in contact with the vertebrae with varieties of shape such as saw tooth notches as described in the patents FR0006351 or FR2733413. Such a solution however proves to be insufficient in a certain number of cases.

Another solution consists of equipping the cage with a flange that extends on the outside of the intervertebral space and is applied on the side of each of the two contiguous vertebrae, to which it is fixed by a bone anchoring screw. Such a solution has been used since about 1988 and is described for example in the patent FR 2 747 034. Such a plate however represents an overcrowding outside the intervertebral space that sometimes may pose problems in particular in the case of arthrodesis of the cervical vertebrae where the space available is very limited. In fact, the presence of the plate may for example form a daily discomfort for the patient or form an immediate or future obstacle in the positioning of another cage with plate in one of the immediately adjacent plates.

Furthermore, in particular in the case of cervical vertebrae, the movements of the spine often have the tendency to cause loosening of the bone anchoring screws, which decreases the effectiveness of such a plate and may also cause damages to the organs surrounding the plate.

Therefore, it is worthwhile to also provide for a system enabling fixation of the cage without a part extending outside the intervertebral space.

Moreover, these different solutions may fulfil the needs of an arthrodesis operation differently without it being necessarily possible to know in advance which will be preferable. Therefore, it is easier and less expensive to provide for a modular device comprising interchangeable parts for achieving different solutions.

To remedy some of these drawbacks, the present invention proposes an intervertebral arthrodesis device designed to be inserted in an intervertebral space separating the opposite plates of the two adjacent vertebrae, characterised in that it comprises at least one structure called intervertebral cage presenting the shape of a ring that may or may not be open, in which at least one part, along the axis of the spine, has a lower height than the rest of this same cage and forms a small bar crossed by at least one drilling of the axis approximately perpendicular to the plate of at least one of the adjacent vertebrae.

According to one characteristic, the device includes at least one intervertebral cage having on its surfaces in contact with the vertebrae, undulations in shape limiting its possibilities for sliding in a plane parallel to said vertebrae.

According to one characteristic, the device comprises at least one fixation structure for fixedly mounting the cage(s) to at least one of these vertebrae. The fixation structure can be added to at least one intervertebral cage by insertion of a projecting part in at least one bore or opening of the cage.

According to one characteristic, the fixation structure includes at least two bone anchoring pins with approximately parallel axes. The pins are connected together by a small rod, and extend through openings or bores of the small rod of the cages. The pins extending through the opening are pushed into a face of at least one vertebra to keep the cage in position in the intervertebral space.

According to one characteristic, at least one of the bone anchoring pins of the fixation structure includes reliefs for limiting the possibilities of the cage sliding outside the face where it is impacted.

According to one characteristic, the fixation structure comprises at least one fixation plate fixed to the external surface of at least one vertebra and including at least one opening or bore for receiving a bone anchoring screw fixed to this same vertebra.

According to one characteristic, at least one of the openings of the fixation plate presents in the plane of this plate a section at the level of its opening opposite the vertebra that is not as high as in its part located within the thickness of the plate. A bone anchoring screw has a head which presents at least one part of a section greater than that of the opening of the plate and is thus retained within this same opening by this same external opening.

According to one feature, the fixation structure includes at least two locking studs with approximately parallel axes connected by a small rod. These locking studs are inserted into at least one hole or bore of at least one intervertebral cage to lock said fixation structure to said cage and to keep the cage in position in the intervertebral space.

According to one feature, at least one of the ends of the small rod has at least one protuberance clipped in at least one housing arranged in the wall of the intervertebral cage so as to limit or prevent the movements of this same rod relative to this same cage.

According to one characteristic, the fixation structure comprises a fixation plate (called a hemiplate) coupled to the exterior surface of at least one vertebra. The fixation plate structure includes at least one opening or bore through which is inserted a bone anchoring screw fixed in other vertebra to keep said cage in position in the intervertebral space.

According to one feature, the fixation hemiplate with the small rod connecting the anchoring pins or the locking studs forms a piece with an "L" section.

According to one characteristic, the fixation structure comprises a fixation plate (called complete) coupled to the exterior surface of at least two vertebrae. Near each end of the plate there is at least one bore or opening through which is inserted a bone anchoring screw that is fixed in said vertebrae to prevent any migration of the intervertebral cage within or outside the intervertebral space.

According to one characteristic, the complete fixation plate with the small rod connects the anchoring pins or the locking studs with a "T" section.

According to one feature, the fixation plate includes an opening at the level of the intervertebral space. This opening enables the introduction or packing of a graft or bone substitute in the intervertebral space after insertion of the device.

According to one characteristic, each bore in the fixation structure acts with a bone anchoring screw. When the anchoring screw is in place, it is located in a position shifted relative to a plane containing the axis of the spine.

According to one feature, at least one intervertebral cage has, along the axis of the spine, a nonuniform height. This variation in height induces a determined angle between the vertebra faces with respect to the adjacent vertebrae.

According to one characteristic, at least one of the constitutive parts of the device is made from a radiotransparent material.

The invention, with its characteristics and advantages, will be more clearly evident with the reading of the description made in reference to the fixed drawings which:

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3C is a perspective view of a device according to a preferred embodiment of the invention before impacting tongues in an embodiment, where the fixation device comprises anchoring tongues;

FIG. 4B is a perspective view of a device according to a preferred embodiment of the invention where the fixation device comprises anchoring pins and a top hemiplate with an opening;

FIG. 5A is a perspective view of a device according to a preferred embodiment of the invention where the fixation device comprises anchoring pins and a complete plate with an opening; and FIG. 5B is a perspective view of a device according to a preferred embodiment of the invention where the fixation device comprises a complete plate added by locking studs, illustrated with anchoring screws.

DETAILED DESCRIPTION

Reference is now made to the Figures wherein is illustrated ring shaped intervertebral cage (1), designed to be inserted in the intervertebral space (E) to be treated between two contiguous vertebrae, and to be received into an interior cavity (10, FIG. 2) a bony material acting as a graft, or any structure that can act as a bony substitute or be "assembled" by a growth of bony material. The cavity of the intervertebral cage can thus be filled before or after it is positioned in the intervertebral space.

According to some applications, the device includes a single intervertebral cage (1, FIGS. 1 and 2), for example to carry out arthrodesis between two cervical vertebrae. It is to be understood that for other applications, the device can include two intervertebral cages (not represented), for example, to carry out arthrodesis between two lumbar vertebrae during positioning by the posterior route.

According to the applications, an intervertebral cage according to the invention may be made in the shape of a closed ring (1, FIG. 3A) or in the form of a ring opened on one side (not represented).

Figure 1A:
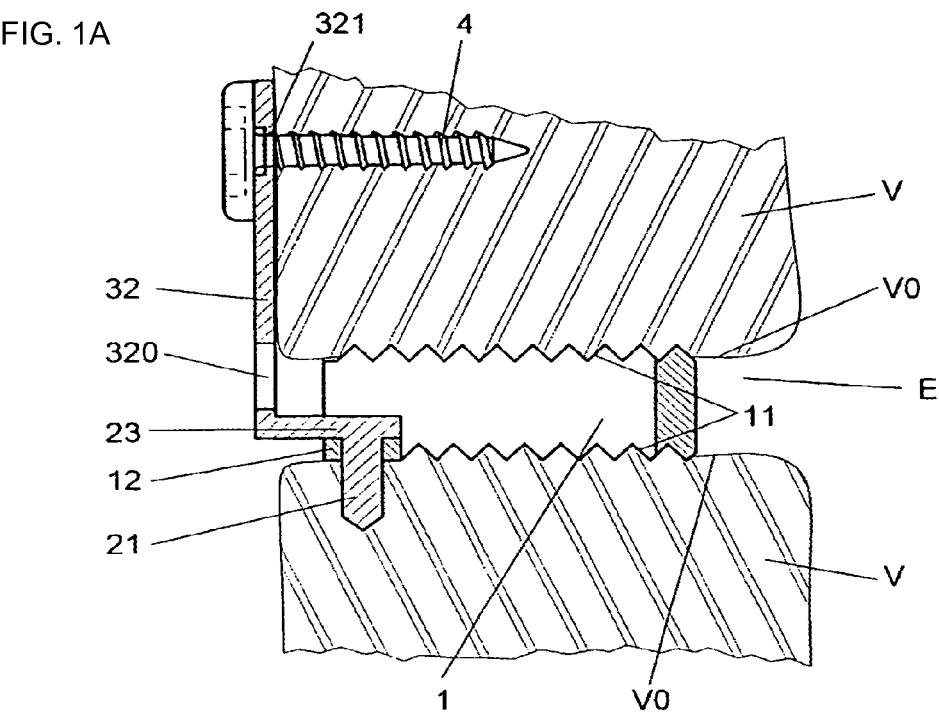
FIG. 1A is a side sectional view of the device according to the invention in an embodiment where the fixation device comprises anchoring pins and a top hemiplate.
Figure 1B:
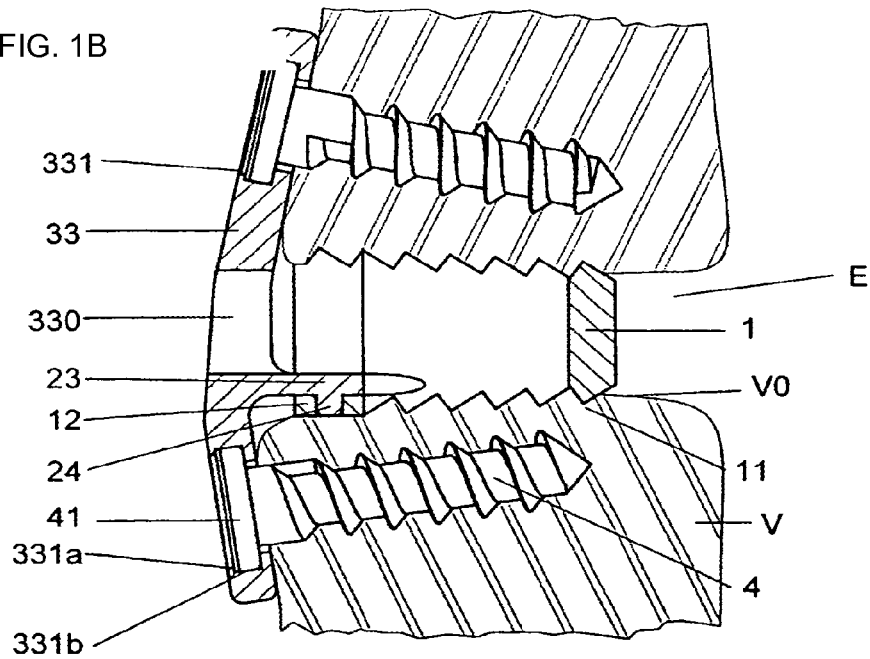
FIG. 1B is a side sectional view of the device according to the invention in an embodiment where the fixation device comprises a complete plate, with opening, added by locking studs and with anchoring screws retained in the openings or bores of the plate.
Figure 2:
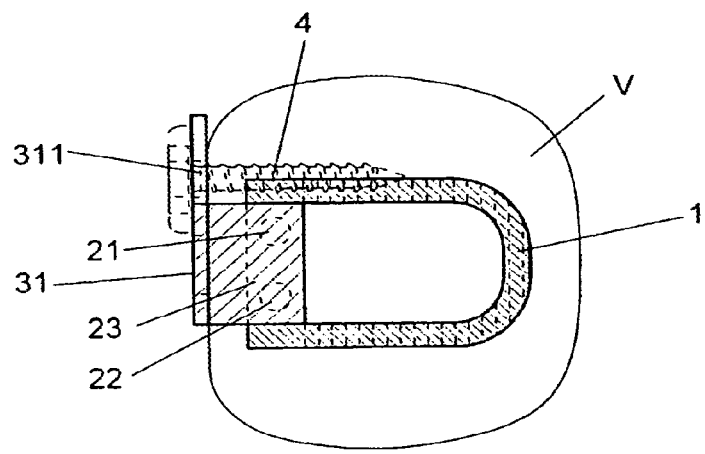
FIG. 2 is a top sectional view of the device according to the invention in an embodiment where the fixation device comprises anchoring pins and a low hemiplate.

In one embodiment represented in FIGS. 1 and 2, the invention comprises a fixation device enabling its anchoring in the plate (V0) of a vertebra (V) within the intervertebral space (E) to be treated. This fixation device is formed from two anchoring pins (21, 22), with approximately parallel axes and connected by a small rod (23). These anchoring pins are introduced into two drillings (121, 122) made in a thinned down part of the intervertebral cage, then are impacted, that is pushed in with force, into the bony material forming the plate of one of the two vertebrae surrounding the intervertebral space to be treated.

In one embodiment, the thinned down part of the cage forms a small flat rod (12) that abuts small flat rod (23), connecting the two anchoring pins (21, 22) when the latter are impacted in face (V0) of a vertebra (V). The thickness of the small rod (23) connecting the anchoring pins and the small rod (12) formed by a thinning of the intervertebral cage (1) are such that the superimposition of the two small rods (12, 23) after impacting is no higher along the axis of the spine than the rest of the intervertebral cage (1).

Figure 3A:
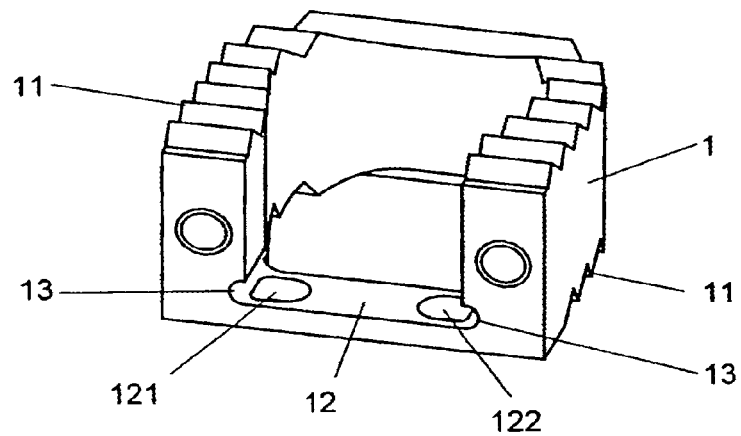
FIG. 3A is a perspective view of an intervertebral cage according to a preferred embodiment of the invention.
Figure 3B:
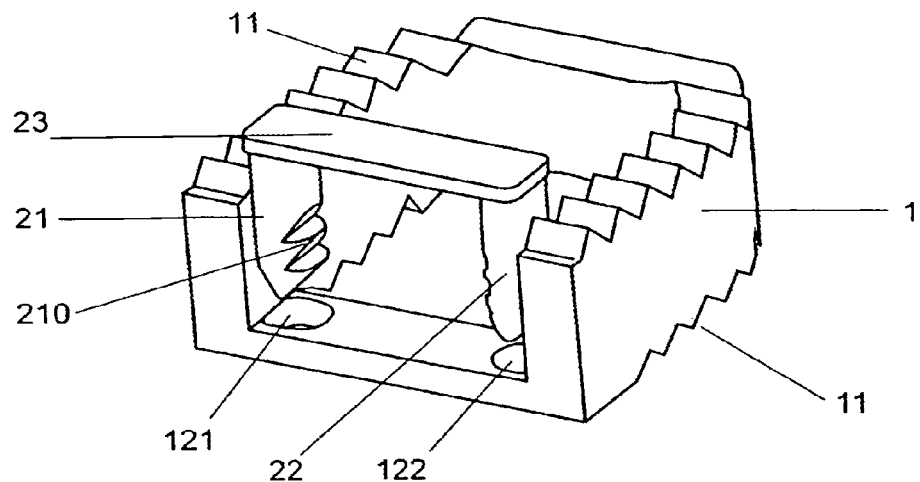
FIG. 3B is a perspective view of a device according to a preferred embodiment of the invention before insertion of impacting pins in an embodiment where the fixation device comprises anchoring pins with undulations in shape.

In one embodiment represented in FIG. 3B the length of the anchoring pins (21, 22) and the thickness of the small rod (23) connecting them are determined so that the sum of these two dimensions forming the height of the fixation device in this embodiment is no greater than the height along the axis of the spine of the rest of the intervertebral cage (1). Thus, it is possible to introduce into this intervertebral space an intervertebral cage already provided with anchoring pins, the latter then only having been impacted into the face (VO) of a vertebra (V), for example with the aid of a spreader, a distractor or another tool of known type.

In one embodiment represented in FIG. 3C, the fixation device, enabling the device to be anchored in the face (V0) of a vertebra (V) within the intervertebral space (E) to be treated, is constituted of an anchoring tongue including legs (51, 52) having intersecting edges forming a "V" are connected by a small rod (53). Legs (51, 52) are introduced between a thinned down part of the intervertebral cage formed by a small rod (62) and two lugs (only one, 54, is represented on FIG. 3C) formed on the device and symmetrically disposed in relation to the device axis. The "V" shaped tongue includes legs (51, 52) is then forced into place similarly to the device provided with pins (21, 22). Legs (51, 52) are forced into place in face V0 of vertebra V so the small flat rod (53), connecting the anchoring legs (51, 52) abuts small flat rod (62). The diameters of the small rod (53) connecting the anchoring tongues and the small rod (62) formed by a thinning of the intervertebral cage (1) are such that the superimposition of the two small rods (62, 53) after legs (51, 52) are forced into face (V0) is no higher along the axis of the spine than the rest of the intervertebral cage (1).

In one embodiment (not shown), the device according to the invention comprises two intervertebral cages. Each of the two cages is formed from an open ring having at least one part having a reduced height along the axis of the spinal cord. In one embodiment, at least one of the cages is in the shape of a "U" or "C" (not shown). Each cage includes at its end a small rod from one part having a reduced height along the axis of the spine. These small rods are crossed by at least one bore or opening having an axis approximately perpendicular to the face (V0) of the vertebra (V) with which they are in contact. In one embodiment, two intervertebral cages are arranged in the intervertebral space with their openings facing each other. At least one fixation device including two anchoring pins with parallel axes connected by a small rod is introduced into the bore of each of the two small rods with ends facing each other. The anchoring pins are then forced into the face of the vertebra and inserted into the bores of the small rods of the intervertebral cages to help to keep said cages immovable.

In one embodiment, an intervertebral cage (1) used in a device according to the invention has at least one undulating surface (11) in contact with the vertebrae; in one example, the undulating contact surface (11) has a saw tooth shape as illustrated in FIG. 3C. Under the pressure exerted by the vertebrae surrounding the treated intervertebral space (E), the undulating surface (11) supports the surface of faces (V0) of these same vertebrae to limit the risks of displacement of the intervertebral cage.

In one embodiment, represented in FIGS. 1, 2 and 4B, a fixation device comprises a plate called top hemiplate (32) united with the small rod (23) connecting the anchoring pins (21, 22) to each other. Hemiplate (32) extends outside the intervertebral space (E) to be treated and is coupled to the exterior surface of the vertebra opposite the vertebra receiving the anchoring pins. This top hemiplate (32) includes at least one bore or opening (321) which receives a bone anchoring screw (4) of a known type. Screw (4) is fixed in the body of the vertebra and inserted in the face (V0) to prevent any migration of the intervertebral cage (1) within or outside the treated intervertebral space (E). Top hemiplate (32) also comprises an opening (320) enabling introduction of the graft into the cage (1) after the cage is positioned in the intervertebral space. The part of the piece connecting the small rod (23) and the top hemiplate (32) has an "L" shape.

Figure 4A:
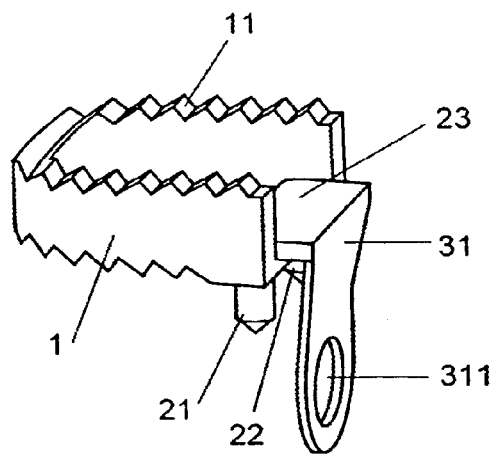
FIG. 4A is a perspective view of a device according to a preferred embodiment of the invention where the fixation device comprises anchoring pins and a low hemiplate.

In one embodiment represented in FIG. 4A, a plate called bottom hemiplate (31), is fixed in the same way to the vertebra receiving the anchoring pins. The part of the piece connecting the small rod (23) and the bottom hemiplate (31) has an "L" shape.

In one embodiment represented in FIG. 5A, a fixation device comprises a plate called complete plate (33) that is integral with the small rod (23) connecting the anchoring pins (21, 22) to each other. Plate (33) extends to the exterior of the intervertebral space (E) to be treated and is coupled to the exterior surface of these two vertebrae surrounding the intervertebral space (E) to be treated. The part of the piece connecting the small rod (23) and the complete plate (33) has a "T" shape. Complete plate (33) includes at least two bores (331, 332), each of which receives a bone anchoring screw (4) of a known type. Screw (4) is fixed in the body of the corresponding vertebra and inserted in the plate (33) to prevent any migration of the intervertebral cage (1) within or outside the treated intervertebral space (E). This complete plate (33) also comprises an opening (330) enabling introduction of the graft into the cage (1) after the cage is placed in the intervertebral space.

In one embodiment represented in FIGS. 1B, 5A and 5B, a fixation device comprises a plate called complete plate (33) united with the small rod (23). Small rod (23) includes two locking studs (24, 25) perpendicular to the longitudinal axis of rod (23). Studs (24, 25) are housed in the two bores (121, 122) of the intervertebral cage (1). This complete plate (33) extends outside the intervertebral space (E) to be treated and is coupled to the exterior surface of the two vertebrae surrounding the intervertebral space (E) to be treated. The use of locking studs (24, 25) rather than pins makes it possible to use a softer material that is forced into the face of the vertebra, but on the other hand has the advantage of being transparent during radiography. The part of the piece connecting the small rod (23) and the complete plate (33) has a "T" shape in its section along a plane containing the axis of the spine.

This complete plate (33) includes at least two bores (331, 332) each of which receives a bone anchoring screw (4) of a known type. Screw (4) is fixed in the body of the corresponding vertebra and inserted into the face of the vertebra to prevent migration of the intervertebral cage (1) within or outside the treated intervertebral space (E).

In the embodiment illustrated in FIGS. 3A and 5A, each of the two opposite ends of the small rod (23) connecting the locking studs and the complete plate (33) has a rounded protuberance contacting the walls of the intervertebral cage (1). The rounded protuberances are clipped by elastic deformation in a housing (13) arranged in the wall opposite the intervertebral cage (1). The clipping of the protuberances (233) in the housings (13) makes it possible to maintain the cage (1) and the plate (33) together during positioning of the unit or after positioning.

In one embodiment, to prevent the anchoring screws from loosening, for example under the effect of the movements of the spine, the bores in plate (33) that receive the screws in a plane parallel to the plate (33) have a section slightly lower than the interior of the plate at the level of their opening on the surface opposite the vertebra; the surface opposite the vertebrae is called an external surface area. The heads of the screws have a part of a section greater than that of the external opening of the bore. Thus, once the screw has been screwed to where the large part of the head of the screw has penetrated the interior of the bore under force, the elasticity of the material forming the plate retains the screw head within the bore, limiting the risks of later loosening. This complete plate (33) also comprises an opening (330) enabling introduction of the graft into the cage (1) after positioning of the cage in the intervertebral space.

In one embodiment the plate (31, 32, 33) of the fixation device includes at least one bore (311, 321, 331, 332) for receiving a bone anchoring screw (4) which is located in a position shifted relative to a plane containing the axis of the spine. Thus, it is possible to treat two adjacent intervertebral spaces by using fixation plates and by positioning these plates in staggered rows. The shifted position of the bores in the plates enables the plates to be fixed in place by different screws located on the same vertebra and at the same height along the axis of the spine.

In one embodiment, all or part of the device according to the invention is made from a radiotransparent material, for example from PEEK, which makes it possible to monitor the development of bony tissues within the cage by radiography. In spite of that, for verification that the elements of the device are not displaced, it is possible to fix one or more of the elements with a radio marker containing, for example, a small piece of non-radiotransparent material.

Therefore, according to the applications it is possible to position an intervertebral cage (1) in different ways, simply by using one type or another of fixation device. The same intervertebral cage (1) can, for example, be positioned:
  either alone,
  or provided with a fixation device with pins (21, 22, 23),
  or provided with a fixation device with pins and a top (32) or bottom (33) hemiplate,
  or provided with a fixation device with pins and with a complete plate (33),
  or provided with a top (32) or bottom (31) hemiplate added by locking studs (24, 25),
  or provided with a complete plate (33) added by locking studs (24, 25).

Such modularity makes it possible for the surgeon to choose the type of fixation during the surgery and according to the anatomic conditions he encounters, by having at his disposal a reduced number of components among which to choose.

The fixation device that includes pins or a plate or both, can be later removed (for example during a new surgery) without significant destruction of the arthrodesis. In fact, this device may no longer be necessary after reinforcement of the arthrodesis, although providing discomfort, either for the patient or for similar treatment of an adjacent intervertebral space.

It must be obvious for persons skilled in the art that the present invention makes possible embodiments under numerous other specific forms without leaving the field of application of the invention as claimed. As a result, the present embodiments must be considered as illustration, but may be modified in the field defined by the scope of the fixed claims, and the invention must not be limited by the details given above.

What is claimed is:

1. A intervertebral cage and anchor combination comprising
   an elongated, rigid anchor comprising a tongue-shaped body, a first end configured for penetration of a vertebral surface, and a second end comprising a protuberance; and
   a ring shaped intervertebral cage having a top, a bottom, a right side, a left side, a front, and a back, the cage comprising,
     a top right vertebral contact surface disposed on the top of the cage along the right side of the cage,
     a top left vertebral contact surface disposed on the top of the cage along the left side of the cage,
     a gap along the back of the cage separating the top right vertebral contact surface and the top left vertebral contact surface,
     a bar extending across the gap and connecting the right side of the cage and the left side of the cage at the back of the cage,
     a first lug extending from the right side of the cage toward the left side of the cage,
     a second lug extending from the left side of the cage toward the right side of the cage, and
     a passage formed by a space between the bar, the first lug, and the second lug and configured to receive the anchor; with
   the anchor and cage having an assembled configuration in which the protuberance of the anchor abuts the passage and the first end of the anchor extends away from the cage.

2. The intervertebral cage and anchor combination of claim 1 in which the cage further comprises a bottom right vertebral contact surface disposed on the bottom of the cage along the right side of the cage and a bottom left vertebral contact surface disposed on the bottom of the cage along the left side of the cage.

3. The intervertebral cage and anchor combination of claim 2 in which the first lug extends the bottom right vertebral contact surface and the second lug extends the bottom left vertebral contact surface.

4. The intervertebral cage and anchor combination of claim 3 in which the bar connects the bottom right vertebral contact surface and the bottom left vertebral contact surface.

5. The intervertebral cage and anchor combination of claim 4 in which the gap extends from the top of the cage to the bar.

6. The intervertebral cage and anchor combination of claim 1 in which the first end of the anchor comprises a "V" shaped notch.

7. The intervertebral cage and anchor combination of claim 1 in which the protuberance of the anchor has the shape of a rod.

8. The intervertebral cage and anchor combination of claim 1 in which the right side of the cage and the left side of the cage have nonuniform heights.

9. The intervertebral cage and anchor combination of claim 8 in which the cage has a height at the gap that is less that the heights of the right side of the cage and the left side of the cage at the back of the cage.

10. The intervertebral cage and anchor combination of claim 1 in which the first lug and the second lug are oriented collinearly.

11. A vertebral fusion device comprising:
  a rigid anchor comprising a tongue-shaped body and an end formed with a protuberance;
  a ring shaped cage formed with a rounded nose and opposed side walls each comprising upper and lower vertebral support surfaces extending from the nose, with the opposed side walls connected at a back end of the cage opposite the rounded nose by a bar, and with the back end of the cage having a height less than a height of the opposed side walls at the back end of the cage; and
  an anchor passage formed by a space between the bar and lugs extending from the opposed side walls, the anchor passage being configured to accommodate the tongue shaped body of the anchor with the protuberance of the anchor abutting the passage.

12. The vertebral fusion device of claim 11 in which the lugs extend the lower vertebral support surfaces of the opposed side walls.

13. The vertebral fusion device of claim 12 in which the bar connects the lower vertebral support surfaces of the opposed side walls.

14. The vertebral fusion device of claim 11 in which the upper vertebral support surfaces of the opposed side walls are separated by a gap at the back end of the cage.

15. The vertebral fusion device of claim 14 in which the gap is bounded by the bar.

16. The vertebral fusion device of claim 15 in which the lugs are oriented collinearly.

17. The vertebral fusion device of claim 16 in which the opposed side walls have nonuniform heights.

18. The vertebral fusion device of claim 17 in which the protuberance of the anchor has the shape of a rod.

19. The vertebral fusion device of claim 18 in which the anchor has an end that comprises a "V" shaped notch.

20. An intervertebral device for insertion into a spine, the device comprising: an elongated receptacle configured to receive from an edge of the device an elongated, rigid anchor having a tongue-like body and to project a vertebral insertion end of the anchor from an upper or lower side of the device; and a housing configured to receive a protuberance on the anchor and hold the device against the anchor.

\* \* \* \* \*